US010001465B2

(12) United States Patent
Mitchell (10) Patent No.: US 10,001,465 B2
(45) Date of Patent: *Jun. 19, 2018

(54) REAL TIME MEASUREMENT OF MUD LOGGING GAS ANALYSIS (71) Applicant: Halliburton Energy Services, Inc., Houston, TX (US)

(72) Inventor: Ian David Campbell Mitchell, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/374,647

(22) PCT Filed: Sep. 25, 2013

(86) PCT No.: PCT/US2013/061679
§ 371 (c)(1),
(2) Date: Jul. 25, 2014

(87) PCT Pub. No.: WO2015/047249
PCT Pub. Date: Apr. 2, 2015

(65) Prior Publication Data
US 2015/0260703 A1    Sep. 17, 2015

(51) Int. Cl.
*G01N 33/28* (2006.01)
*E21B 49/00* (2006.01)
(Continued)

(52) U.S. Cl.
CPC ......... *G01N 33/2823* (2013.01); *E21B 47/00* (2013.01); *E21B 47/102* (2013.01); *E21B 49/005* (2013.01)

(58) Field of Classification Search
CPC ...... E21B 47/102; E21B 47/00; E21B 49/005; G01N 21/85; G01N 33/2823; G01N 21/15;
(Continued)

(56) References Cited

U.S. PATENT DOCUMENTS 5,167,149 A    12/1992  Mullins et al.
6,176,323 B1 *  1/2001  Weirich .................. E21B 21/08
                                                                175/40
(Continued)

FOREIGN PATENT DOCUMENTS

WO    2015047249 A1    4/2015

OTHER PUBLICATIONS

International Search Report and Written Opinion for PCT/US2013/061679 dated Jun. 20, 2014.

*Primary Examiner* — Natalie Huls
*Assistant Examiner* — Monica S Young
(74) *Attorney, Agent, or Firm* — McDermott Will & Emery LLP (57) ABSTRACT Disclosed are systems and methods for measuring the gas content in drilling fluids in real time using optical computing devices. One system includes a flow path circulating a drilling fluid into and out of a borehole during drilling operations, a first optical computing device arranged at or near an outlet of the borehole and having a first integrated computational element configured to optically interact with the drilling fluid as it exits the borehole and generate a first output signal corresponding to a concentration of a gas present in the drilling fluid at the outlet of the borehole, and a signal processor communicably coupled to the first optical computing device and configured to receive the first output signal and determine the concentration of the gas present in the drilling fluid at the outlet of the borehole.

20 Claims, 3 Drawing Sheets (51) Int. Cl.
*E21B 47/00* (2012.01)
*E21B 47/10* (2012.01)

(58) Field of Classification Search
CPC . G01N 21/3577; G01N 21/359; G01N 21/552
USPC ........................................................ 73/19.09
See application file for complete search history.

(56) References Cited

U.S. PATENT DOCUMENTS

| | | | |
|---|---|---|---|
| 8,812,238 B2* | 8/2014 | Ljungdahl | E21B 49/005 702/12 |
| 2006/0142955 A1* | 6/2006 | Jones | E21B 47/102 702/32 |
| 2009/0008560 A1* | 1/2009 | Gunn | G01N 21/3504 250/343 |
| 2009/0293605 A1* | 12/2009 | Evrard | E21B 49/005 73/152.25 |
| 2010/0148785 A1* | 6/2010 | Schaefer | G01V 8/02 324/338 |
| 2011/0139464 A1* | 6/2011 | Henderson | E21B 21/01 166/370 |
| 2011/0197662 A1* | 8/2011 | McAlister | G01N 1/405 73/61.59 |
| 2011/0313670 A1 | 12/2011 | DeGreeve et al. | |
| 2012/0137764 A1* | 6/2012 | Lawrence | E21B 49/005 73/152.23 |
| 2012/0150451 A1 | 6/2012 | Skinner et al. | |
| 2012/0211650 A1* | 8/2012 | Jones | E21B 49/10 250/269.1 |
| 2013/0031964 A1* | 2/2013 | Tunheim | G01N 21/85 73/61.48 |
| 2013/0033702 A1 | 2/2013 | Tunheinn et al. | |
| 2016/0115786 A1* | 4/2016 | Breviere | E21B 49/08 73/152.23 |

* cited by examiner

REAL TIME MEASUREMENT OF MUD LOGGING GAS ANALYSIS

BACKGROUND

The present disclosure relates to systems and methods for monitoring drilling fluids and, more specifically, for measuring the gas content in drilling fluids in real time using optical computing devices.

During the drilling of a hydrocarbon-producing well, a drilling fluid or "mud" is continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to provide hydrostatic pressure on the walls of the drilled borehole to prevent wellbore collapse and the resulting influx of gas or liquid from the formations being drilled.

Analyzing the drilling fluid as it returns to the surface is recognized in the oil and gas industry as an important first appraisal of a potential hydrocarbon-bearing reservoir zone, thereby providing important data to guide subsequent evaluation and testing. Such analysis and testing is commonly referred to as "mud logging" analysis. Through mud logging, reservoir zones can be evaluated while they are being initially penetrated, thereby substantially preventing post-drilling changes to the formation that can limit the effectiveness of many other evaluation techniques.

Mud logging often includes the measurement and analysis of formation gases present in the drilling fluid as it returns to the surface. Such analysis can be valuable in providing data on the hydrocarbon and non-hydrocarbon gas species that may be encountered while drilling. Specifically, knowing the presence and concentration of hydrocarbon and non-hydrocarbon gases in drilling fluids provides an indication of the formation confronted by the drill bit and provides a basis for determining the feasibility of obtaining hydrocarbons from the well. The information that such analysis provides is vital in the planning and development of hydrocarbon reservoirs, as well as in the assessment of a reservoir's capacity and performance.

Mud logging analysis of drilling fluids is typically conducted off-line using laboratory analyses which require the extraction of a sample of the drilling fluid and a subsequent controlled testing procedure usually conducted at a separate location. Depending on the analysis required, however, such an approach can take hours to days to complete, and even in the best case scenario, a job will often be completed prior to the analysis being obtained. Although off-line, retrospective analyses can be satisfactory in certain cases, they nonetheless do not allow real-time or near real-time analysis capabilities. As a result, proactive control of drilling operations cannot take place, at least without significant process disruption occurring while awaiting the results of the analysis. Off-line, retrospective analyses can also be unsatisfactory for determining true characteristics of a drilling fluid since the characteristics of the extracted sample of the drilling fluid oftentimes change during the lag time between collection and analysis, thereby making the properties of the sample non-indicative of the true chemical composition or characteristic.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to systems and methods for monitoring drilling fluids and, more specifically, for measuring the gas content in drilling fluids in real time using optical computing devices.

The exemplary systems and methods described herein employ various configurations and arrangements of optical computing devices, also commonly referred to as "opticoanalytical devices," for the real-time or near real-time monitoring of a fluid, such as a drilling fluid or a completion fluid. In operation, the exemplary systems and methods may be useful and otherwise advantageous in determining one or more properties or characteristics of the fluid, such as the type and concentration of one or more gases present within the fluid. The optical computing devices can advantageously provide real-time fluid monitoring that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, thereby allowing qualitative and/or quantitative analyses of the fluid to occur without having to extract a sample and undertake time-consuming analyses of the sample at an off-site laboratory.

The systems and methods disclosed herein may be suitable for use in the oil and gas industry since the described optical computing devices provide a cost-effective, rugged, and accurate means for monitoring oil/gas-related fluids, such as drilling fluids. In particular, the systems and methods may prove advantageous for use in mud logging gas analysis, thereby providing continuous data on the hydrocarbon and non-hydrocarbon gas species that may be encountered while drilling boreholes for the exploitation of hydrocarbon reserves below the earth's surface. When the drilling fluid returns to the surface, for example, it may contain the hydrocarbons (and other compounds) contained within the rock that has been drilled as well as additional hydrocarbons that have leaked into the wellbore from the surrounding rock formation. The real-time measurement of the abundance of these gas compounds will yield information on the hydrocarbon content of the rock.

By measuring the gas content directly in the drilling fluid, it is not necessary to extract a gas sample from the fluid for mud logging gas analysis. This may prove particularly advantageous as the gas extraction process normally used in mud logging gas analyses is not efficient, since it depends on a number of variables including temperature, flow rate, viscosity, drilling fluid type, etc. Using the optical computing devices described herein will effectively eliminate all these variables from the analysis. By reducing variation in the analysis, the accuracy of the results may greatly increase. The reliability is also improved since there are fewer moving parts. In addition, using the optical computing devices described herein dramatically reduces the lag time between drilling fluid exiting the wellhead and the measurement results being available. Update rates are also greatly improved over traditional extraction systems.

The optical computing devices can be deployed at various points within a drilling fluid circulation system to monitor the drilling fluid and its associated gas content. Depending on the location of the particular optical computing device, different types of information about the fluid can be obtained. In some cases, for example, the optical computing devices can be used to monitor the type and concentration of gases therein before and after the drilling fluid circulates into and out of a wellbore. In other cases, the optical computing devices may be used to monitor the effectiveness of a degassing system used to remove gases from the drilling fluid following its return to the system. In yet other cases, the optical computing devices may be used to analyze an extracted gas sample in real-time following its extraction from the drilling fluid. In other cases, the optical computing devices may be used to monitor the drilling fluid at a point before a choking device so as to register real-time gas concentrations of the drilling fluid while circulating at wellbore conditions.

As used herein, the term "fluid" refers to any substance that is capable of flowing, including particulate solids, liquids, gases, slurries, emulsions, powders, muds, mixtures, combinations thereof, and the like. In some embodiments, the fluid is a drilling fluid or drilling "mud," including water-based drilling fluids, oil-based drilling fluids, synthetic drilling fluids, and the like. In other embodiments, the fluid is a completion fluid or clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "characteristic" refers to a chemical, mechanical, or physical property of the fluid. A characteristic of the fluid may include a quantitative value or concentration of one or more chemical constituents or compounds present within the fluid. Such chemical constituents may be referred to herein as "analytes." Illustrative characteristics of a substance that can be monitored with the optical computing devices disclosed herein can include, for example, chemical composition (e.g., identity and concentration in total or of individual components or compounds), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc), and the like.

Moreover, the phrase "characteristic of interest of/in a fluid" may be used herein to refer to the concentration or characteristic of a gas contained in or otherwise entrained within the fluid. Exemplary gases that may be monitored or otherwise measured with the optical computing devices as contained within a drilling fluid, for example, include, but are not limited to, methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid and produce an output of electromagnetic radiation from a processing element arranged within the optical computing device. The processing element may be, for example, an integrated computational element (ICE), also known as a multivariate optical element (MOE), used in the optical computing device. The electromagnetic radiation that optically interacts with the processing element is changed so as to be readable by a detector, such that an output of the detector can be correlated to a characteristic of the fluid, such as the type and concentration of a gas in the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements or multivariate optical elements), a fluid, or a gas present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid or a gas of the fluid.

The exemplary systems and methods described herein will include at least one optical computing device arranged along or in a flow path in order to monitor a fluid contained therein. Each optical computing device may include an electromagnetic radiation source, at least one processing element (e.g., an integrated computational element), and at least one detector arranged to receive optically interacted light from the at least one processing element or the fluid. In some embodiments, the exemplary optical computing devices may be specifically configured for detecting, analyzing, and quantitatively measuring a particular characteristic of the fluid, such as the type and concentration of a gas present within the fluid. In other embodiments, the optical computing devices may be general purpose optical devices, with post-acquisition processing (e.g., through computer means) being used to specifically detect the characteristic of the fluid.

The optical computing devices described herein can perform calculations (analyses) in real-time or near real-time without the need for time-consuming sample processing. Moreover, the optical computing devices can be specifically configured to detect and analyze particular characteristics of a fluid or a gas present within the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic of the fluid.

The optical computing devices can be configured to detect not only the composition and concentrations of a gas within a fluid, but they also can be configured to determine physical properties and other characteristics of the fluid and/or the gas based on an analysis of the electromagnetic radiation received from the fluid and/or the gas. For example, the optical computing devices can be configured to determine the concentration of an analyte and correlate the determined concentration to a characteristic of the fluid. As will be appreciated, the optical computing devices may be configured to detect as many characteristics (e.g., gas compounds and their respective concentrations) of the fluid as desired. Monitoring of multiple characteristics requires the incorporation of suitable processing and detection means within the optical computing device for each characteristic. In some embodiments, the properties of the fluid can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or gas will be determined.

The optical computing devices described herein utilize electromagnetic radiation to perform calculations, as opposed to the hardwired circuits of conventional electronic processors. When electromagnetic radiation interacts with a fluid, unique physical and chemical information about the fluid is encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics or analytes within a fluid, and converting that information into a detectable output relating to one or more characteristics of the fluid or a gas present within the fluid. That is, through suitable configurations of the optical computing devices, electromagnetic radiation associated with a characteristic or analyte of interest of a fluid can be separated from electromagnetic radiation associated with all other components of the fluid in order to estimate the properties of the fluid in real-time or near real-time.

Figure 1:
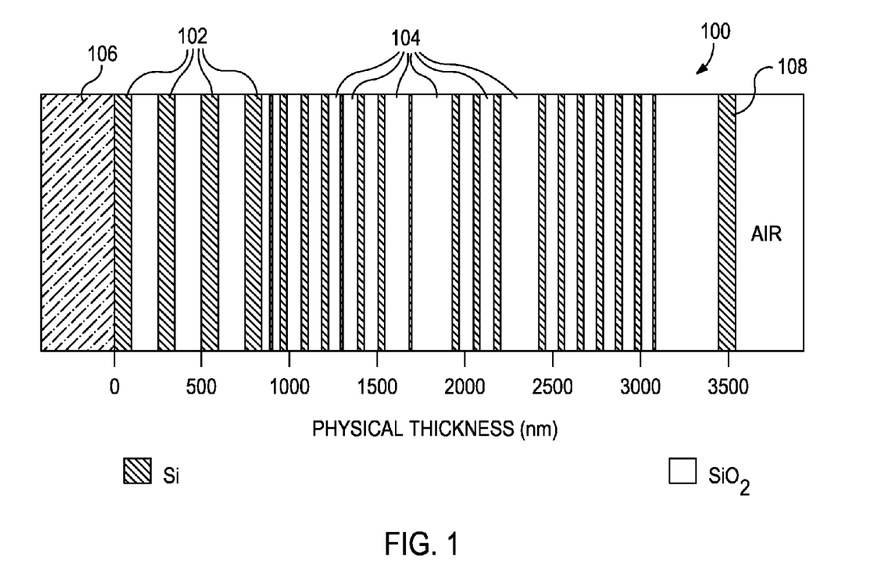
FIG. 1 illustrates an exemplary integrated computation element, according to one or more embodiments.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and SiO$_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and SiO$_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest.

Figure 2:
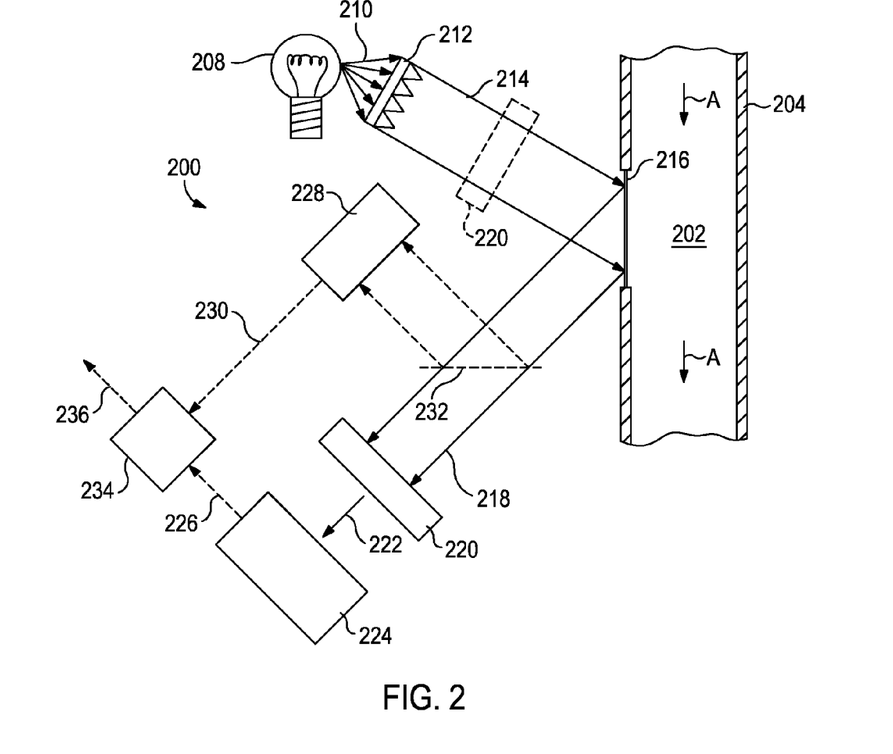
FIG. 2 illustrates an exemplary optical computing device for monitoring a fluid, according to one or more embodiments.

Referring now to FIG. 2, illustrated is an exemplary optical computing device 200 for monitoring a fluid 202, according to one or more embodiments. In the illustrated embodiment, the fluid 202 may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing in the general direction indicated by the arrows A (i.e., from upstream to downstream). Portions of the flow path 204 may be arranged substantially vertical, substantially horizontal, or any directional configuration therebetween, without departing from the scope of the disclosure.

The optical computing device 200 may be configured to determine a characteristic of interest in the fluid 202, such as the type and/or concentration of a gas present within the fluid 202. In some embodiments, the device 200 may include an electromagnetic radiation source 208 configured to emit or otherwise generate electromagnetic radiation 210. The electromagnetic radiation source 208 may be any device capable of emitting or generating electromagnetic radiation, as defined herein. For example, the electromagnetic radiation source 208 may be a light bulb, a light emitting diode (LED), a laser, a blackbody, a photonic crystal, an X-Ray source, combinations thereof, or the like. In some embodiments, a lens 212 may be configured to collect or otherwise receive the electromagnetic radiation 210 and direct a beam 214 of electromagnetic radiation 210 toward the fluid 202. The lens 212 may be any type of optical device configured to transmit or otherwise convey the electromagnetic radiation 210 as desired, such as a normal lens, a Fresnel lens, a diffractive optical element, a holographic graphical element, a mirror (e.g., a focusing mirror), or a type of collimator. In other embodiments, the lens 212 may be omitted from the device 200 and the electromagnetic radiation 210 may instead be directed toward the fluid 202 directly from the electromagnetic radiation source 208.

In one or more embodiments, the device 200 may also include a sampling window 216 arranged adjacent to or otherwise in contact with the fluid 202 for detection purposes. The sampling window 216 may be made from a variety of transparent, rigid or semi-rigid materials that are configured to allow transmission of the electromagnetic radiation 210 therethrough. For example, the sampling window 216 may be made of, but is not limited to, glasses, plastics, semi-conductors, crystalline materials, polycrystalline materials, hot or cold-pressed powders, combinations thereof, or the like. After passing through the sampling window 216, the electromagnetic radiation 210 impinges upon and optically interacts with the fluid 202. As a result, optically interacted radiation 218 is generated by and reflected from the fluid 202. Those skilled in the art, however, will readily recognize that alternative variations of the device 200 may allow the optically interacted radiation 218 to be generated by being transmitted, scattered, diffracted, absorbed, emitted, or re-radiated by and/or from the fluid 202, without departing from the scope of the disclosure.

The optically interacted radiation 218 generated by the interaction with the fluid 202 may be directed to or otherwise be received by an ICE 220 arranged within the device 200. The ICE 220 may be a spectral component substantially similar to the ICE 100 described above with reference to FIG. 1. Accordingly, in operation the ICE 220 may be configured to receive the optically interacted radiation 218 and produce modified electromagnetic radiation 222 corresponding to a particular characteristic of the fluid 202. In particular, the modified electromagnetic radiation 222 is electromagnetic radiation that has optically interacted with the ICE 220, whereby an approximation of the regression vector corresponding to the characteristic of the fluid 202 is obtained.

While FIG. 2 depicts the ICE 220 as receiving reflected electromagnetic radiation from the fluid 202, the ICE 220 may be arranged at any point along the optical train of the device 200, without departing from the scope of the disclosure. For example, in one or more embodiments, the ICE 220 (as shown in dashed) may be arranged within the optical train prior to the sampling window 216 and equally obtain substantially the same results. In other embodiments, the ICE 220 may generate the modified electromagnetic radiation 222 through reflection, instead of transmission therethrough.

Moreover, while only one ICE 220 is shown in the device 200, embodiments are contemplated herein which include the use of at least two ICE components in the device 200 configured to cooperatively determine the characteristic of interest in the fluid 202. For example, two or more ICE may be arranged in series or parallel within the device 200 and configured to receive the optically interacted radiation 218 and thereby enhance sensitivities and detector limits of the device 200. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time. The two or more ICE components in any of these embodiments may be configured to be either associated or disassociated with the characteristic of interest in the fluid 202. In other embodiments, the two or more ICE may be configured to be positively or negatively correlated with the characteristic of interest in the fluid 202.

In some embodiments, it may be desirable to monitor more than one characteristic of interest at a time using the device 200, such as detecting multiple types or compounds of gases within the fluid 202. In such embodiments, various configurations for multiple ICE components can be used, where each ICE component is configured to detect a particular and/or distinct characteristic of interest. In some embodiments, the characteristic can be analyzed sequentially using multiple ICE components that are provided a single beam of electromagnetic radiation being reflected from or transmitted through the fluid 202. In some embodiments, multiple ICE components can be arranged on a rotating disc, where the individual ICE components are only exposed to the beam of electromagnetic radiation for a short time. Advantages of this approach can include the ability to analyze multiple characteristics of the fluid 202 using a single optical computing device 200 and the opportunity to assay additional characteristics (e.g., types or compounds of gases within the fluid 202) simply by adding additional ICE components to the rotating disc.

In other embodiments, multiple optical computing devices can be placed at a single location along the flow path 204, where each optical computing device contains a unique ICE that is configured to detect a particular characteristic of interest in the fluid 202. In such embodiments, a beam splitter can divert a portion of the electromagnetic radiation being reflected by, emitted from, or transmitted through the fluid 202 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 204. Likewise, multiple detection stations, each containing optical computing devices in parallel, can be placed in series for performing a similar analysis.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce an output signal 226 in real-time or near real-time in the form of a voltage (or current) that corresponds to the particular characteristic of interest in the fluid 202. The voltage returned by the detector 224 is essentially the dot product of the optical interaction of the optically interacted radiation 218 with the respective ICE 220 as a function of the concentration of the characteristic of interest of the fluid 202. As such, the output signal 226 produced by the detector 224 and the concentration of the characteristic may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 208. Undesirable radiating deviations can occur in the intensity of the electromagnetic radiation 210 due to a wide variety of reasons and potentially causing various negative effects on the device 200. These negative effects can be particularly detrimental for measurements taken over a period of time. In some embodiments, radiating deviations can occur as a result of a build-up of film or material on the sampling window 216 which has the effect of reducing the amount and quality of light ultimately reaching the first detector 224. Without proper compensation, such radiating deviations could result in false readings and the output signal 226 would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signal 226 generated by the first detector 224. As illustrated, the second detector 228 may be configured to receive a portion of the optically interacted radiation 218 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 224, 228. The signal processor 234 may be a computer including a processor and a machine-readable storage medium having instructions stored thereon, which, when executed by the processor 234, cause the optical computing device 200 to perform a number of operations, such as determining a characteristic of interest of the fluid 202. For instance, the concentration of each characteristic detected with the optical computing device 200 can be fed into an algorithm operated by the signal processor 234. The algorithm can be part of an artificial neural network configured to use the concentration of each detected characteristic in order to evaluate the overall characteristic(s) or quality of the fluid 202.

The signal processor 234 may also be configured to computationally combine the compensating signal 230 with the output signal 226 in order to normalize the output signal 226 in view of any radiating deviations detected by the second detector 228. Computationally combining the output and compensating signals 220, 228 may entail computing a ratio of the two signals 220, 228. For example, the concentration or magnitude of each characteristic determined using the optical computing device 200 can be fed into an algorithm run by the signal processor 234. The algorithm may be configured to make predictions on how the characteristics of the fluid 202 change if the concentrations of one or more components or additives are changed relative to one another.

In real-time or near real-time, the signal processor 234 may be configured to provide a resulting output signal 236 corresponding to a characteristic of interest in the fluid 202, such as the concentration of a gas present in the fluid 202. The resulting output signal 236 may be readable by an operator who can consider the results and make proper adjustments or take appropriate action, if needed. In some embodiments, the resulting signal output 328 may be conveyed, either wired or wirelessly, to an operator for consideration. In other embodiments, the resulting output signal 236 may be recognized by the signal processor 234 as being within or without a predetermined or preprogrammed range of suitable operation and may alert the operator of an out of range reading so appropriate corrective action may be taken, or otherwise autonomously undertake the appropriate corrective action such that the resulting output signal 236 returns to a value within the predetermined or preprogrammed range of suitable operation.

Figure 3:
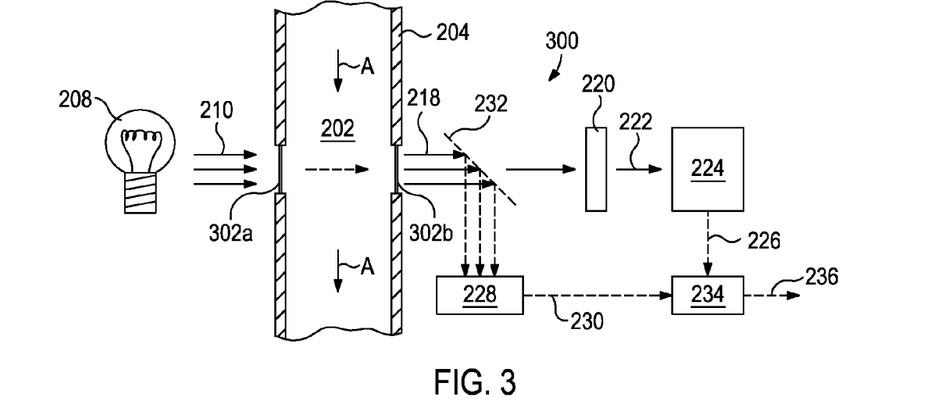
FIG. 3 illustrates another exemplary optical computing device for monitoring a fluid, according to one or more embodiments.

Referring now to FIG. 3, illustrated is another exemplary optical computing device 300 for monitoring the fluid 202, according to one or more embodiments. The optical computing device 300 may be similar in some respects to the optical computing device 200 of FIG. 2, and therefore may be best understood with reference thereto where like numerals indicate like elements that will not be described again. Again, the optical computing device 300 may be configured to determine the concentration of a characteristic of interest in the fluid 202, such as the concentration of a gas within the fluid 202, as contained within the flow path 204. Unlike the device 200 of FIG. 2, however, the optical computing device 300 in FIG. 3 may be configured to transmit the electromagnetic radiation 210 through the fluid 202 via a first sampling window 302*a* and a second sampling window 302*b* arranged radially-opposite the first sampling window 302*a* on the flow path 204. The first and second sampling windows 302*a,b* may be similar to the sampling window 316 described above in FIG. 2 and therefore will not be described again.

As the electromagnetic radiation 210 passes through the fluid 202 via the first and second sampling windows 302*a,b*, it optically interacts with the fluid 202 and optically interacted radiation 218 is subsequently directed to or otherwise received by the ICE 220 as arranged within the device 300. It is again noted that, while FIG. 3 depicts the ICE 220 as receiving the optically interacted radiation 218 as transmitted through the sampling windows 302*a,b*, the ICE 220 may equally be arranged at any point along the optical train of the device 300, without departing from the scope of the disclosure. For example, in one or more embodiments, the ICE 220 may be arranged within the optical train prior to the first sampling window 302*a* and equally obtain substantially the same results. In yet other embodiments, the ICE 220 may generate the modified electromagnetic radiation 222 through reflection, instead of transmission therethrough. Moreover, as with the device 200 of FIG. 2, embodiments are contemplated herein which include the use of at least two ICE components in the device 300 configured to cooperatively determine the characteristic of interest in the fluid 202.

The modified electromagnetic radiation 222 generated by the ICE 220 is subsequently conveyed to the detector 224 for quantification of the signal and generation of the output signal 226 which corresponds to the particular characteristic of interest in the fluid 202. The device 300 may also include the second detector 228 for detecting radiating deviations stemming from the electromagnetic radiation source 208. As illustrated, the second detector 228 may be configured to receive a portion of the optically interacted radiation 218 via the beamsplitter 232 in order to detect the radiating deviations. The output signal 226 and the compensating signal 230 may then be conveyed to or otherwise received by the signal processor 234 which may computationally combine the two signals 230, 226 and provide in real-time or near real-time the resulting output signal 236 corresponding to the concentration of the characteristic of interest in the fluid 202.

Figure 4:
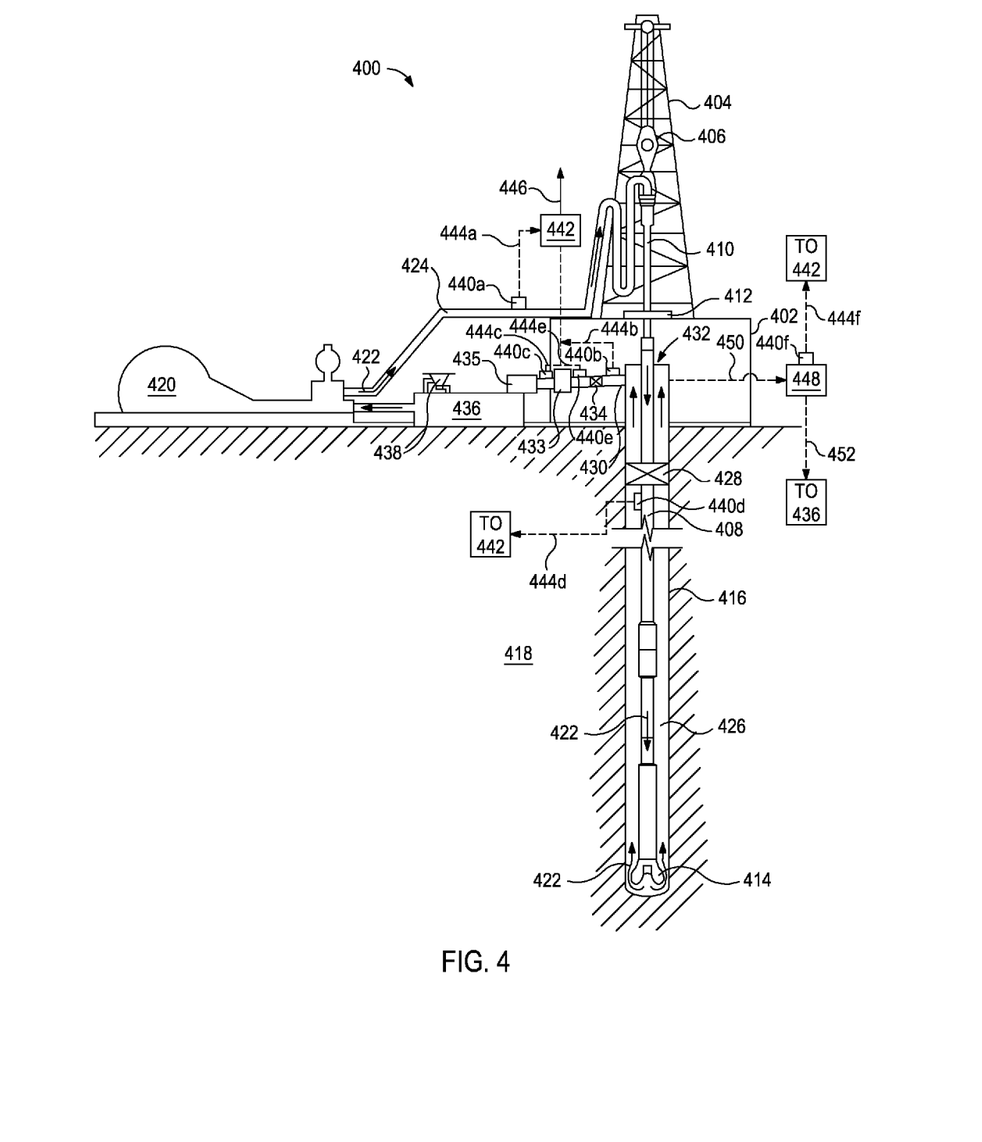
FIG. 4 illustrates an exemplary wellbore drilling assembly that may employ one or more optical computing devices for monitoring a fluid, according to one or more embodiments.

Those skilled in the art will readily appreciate the various and numerous applications that the optical computing devices 200, 300, and various alternative configurations thereof, may be suitably used with. For example, referring now to FIG. 4, illustrated is an exemplary wellbore drilling assembly 400 that may employ one or more of the optical computing devices described herein in order to monitor a drilling fluid or a completion fluid, according to one or more embodiments. The drilling assembly 400 may include a drilling platform 402 that supports a derrick 404 having a traveling block 406 for raising and lowering a drill string 408. A kelly 410 supports the drill string 408 as it is lowered through a rotary table 412. A drill bit 414 is attached to the distal end of the drill string 408 and is driven either by a downhole motor and/or via rotation of the drill string 408 from the well surface. As the bit 414 rotates, it creates a borehole 416 that penetrates various subterranean formations 418.

A pump 420 (e.g., a mud pump) circulates drilling fluid 422 through a feed pipe 424 and to the kelly 410, which conveys the drilling fluid 422 downhole through an interior conduit defined in the drill string 408 and through one or more orifices in the drill bit 414. The drilling fluid 422 is then circulated back to the surface via an annulus 426 defined between the drill string 408 and the walls of the borehole 416. The drilling fluid 422 provides hydrostatic pressure to prevent formation fluids from entering into the borehole 416 and keeps the drill bit 414 cool and clean during drilling. The drilling fluid 422 also serves to carry drill cuttings and solids out of the borehole 416 and suspend the drill cuttings and solids while drilling is paused and/or when the drill bit 414 is brought in and out of the borehole 416.

As the spent drilling fluid 422 returns to the surface, it may pass through one or more wellbore choke valves 428 (one shown) arranged generally within the annulus 426. The wellbore choke valves 428 may be used to reduce and otherwise regulate the fluid pressure of the spent drilling fluid 422 as it is conveyed to the surface for processing and recirculation.

At the surface, the spent drilling fluid 422 may exit the annulus 426 at the wellhead 432 and subsequently pass through one or more surface choke valves 434 (one shown) via an interconnecting flow line 430. The surface choke valve 428 may be used to maintain or otherwise regulate the pressure on the annulus 426 at surface, for example in the range of about 100 psi to about 300 psi. As a result, this will enable drilling to continue underbalanced and is useful in reducing formation 418 damage to the reservoir, but also to facilitate increased drilling speed.

Following the surface choke valve 434, the spent drilling fluid 422 may be conveyed to one or more drilling fluid rehabilitation devices via the interconnecting flow line 430. Such drilling fluid rehabilitation devices may include, but are not limited to, one or more degassing units 433 and one or more solids control equipment 435. The degassing unit 433 may be any device or machine configured to separate from the drilling fluid 422 any gases (i.e., hydrocarbon and non-hydrocarbon gas species) that may have been entrained in the drilling fluid 422 while circulating in and out of the borehole 416. The solids control equipment 435 may be configured to substantially remove the drill cuttings and solids from the drilling fluid 422 and deposit a "cleaned" drilling fluid 422 into a nearby retention pit 436 (i.e., a mud pit).

Several additives or components may be added to the drilling fluid 422 in order to maintain the drilling fluid 422 in proper working order and otherwise enhance drilling capabilities. In some embodiments, the additives and components may be added to the drilling fluid 422 via a mixing hopper 438 coupled to or otherwise in communication with the retention pit 436. Exemplary components that may be added to the drilling fluid 422 include, but are not limited to, emulsions, weighting materials, viscosifiers, thickeners, rheology modifiers, thinners, deflocculants, anionic polyelectrolytes (e.g., acrylates, polyphosphates, lignosulfonates, tannic acid derivates, etc.), high-heat polymers, clay stabilizers, clay inhibitors, tar treatments, water and other base fluids, combinations thereof, and the like. The rehabilitated drilling fluid 422 may then be recirculated and pumped back into the borehole 416 with the pump 420 via the feed pipe 424.

According to the present disclosure, mud logging gas analysis of the drilling fluid 422 may be undertaken by placing one or more optical computing devices 440 (shown as optical computing devices 440a, 440b, 440c, 440d, and 440e) at various predetermined monitoring locations in the circulation system of the drilling assembly 400. The optical computing devices 440a-e may be substantially similar to at least one of the optical computing devices 200, 300 of FIGS. 2 and 3, respectively, and therefore will not be described again in detail. In exemplary operation, the optical computing devices 440a-e may be configured to measure and report real-time characteristics of the drilling fluid 422, such as the type and/or concentration of one or more gases present therein at their respective monitoring locations.

In one or more embodiments, the optical computing devices 440a-e may be communicably coupled to a signal processor 442 and configured to convey corresponding output signals 444a-e, respectively, to the signal processor 442. The signal processor 442 may be similar to the signal processor 234 of FIGS. 2 and 3 and may be configured to receive and process the output signals 444a-e. In some embodiments, the signal processor 442 may employ an algorithm configured to calculate or otherwise determine any differences between any two or more of the output signals 444a-e. For example, the first output signal 444a may be indicative of the type/concentration of a gas in the drilling fluid 422 or another characteristic of the fluid 422 at the location of the first optical computing device 440a, the second output signal 444b may be indicative of the type/concentration of the gas or another characteristic of the fluid 422 at the location of the second optical computing device 440b, and so on. Accordingly, the signal processor 442 may be configured to not only determine the concentration of a gas at each monitoring location but also determine how the concentration of the gas and/or the magnitude of the characteristic of interest in the fluid 422 has changed between each monitoring location.

In real-time or near real-time, the signal processor 442 may be configured to provide a resulting output signal 446 corresponding to one or more characteristics of the fluid 422. In some embodiments, the resulting output signal 446 may provide a measured difference in the gas content and/or the magnitude of the characteristic of interest in the fluid 422. In some embodiments, the resulting output signal 446 may be conveyed, either wired or wirelessly, to an operator for consideration.

In other embodiments, the resulting output signal 446 may be recognized by the signal processor 442 as being within or without a predetermined or preprogrammed range of suitable operation for the drilling fluid 422. If the resulting output signal 446 exceeds the predetermined or preprogrammed range of operation, the signal processor 442 may be configured to alert the operator so appropriate corrective action may be taken on the drilling fluid 422. Otherwise, the signal processor 442 may be configured to autonomously undertake the appropriate corrective action such that the resulting output signal 446 returns to a value within the predetermined or preprogrammed range of suitable operation. At least one corrective action that may be undertaken may include adding additional additives or components to the drilling fluid 422 via, for example, the mixing hopper 438.

As illustrated, a first optical computing device 440a may be arranged to monitor the drilling fluid 422 as it is being introduced into the borehole 416 and a second optical computing device 440b may be arranged to monitor the drilling fluid 422 as it returns to the surface and otherwise exits out of the borehole 416 via the annulus 426. More particularly, the first optical computing device 440a may be arranged in the feed pipe 424 leading to the derrick 404 from the pump 420 (or otherwise at any fluidly communicable location following the pump 420 and before the borehole 416), and the second optical computing device 440b may be arranged on or otherwise coupled to the flow line 430 before the surface choke valve 434. As will be appreciated, more than one optical computing device may be arranged at each of these monitoring locations, without departing from the scope of the disclosure.

By consulting the output signal 444b of the second optical computing device 440b, an operator may be able to determine the type and/or concentration of one or more gases present in the returning drilling fluid 422 in real or near real-time. As a result, the operator may be able to conduct mud logging gas analyses of the drilling fluid 422 without having to extract a gas sample from the returning drilling fluid 422. In some embodiments, the second optical computing device 440b may further be configured to monitor the drilling fluid for hazardous, corrosive, or otherwise toxic gases that may pose a danger to rig operators and others on the surface. For instance, in at least one embodiment, the output signal 444b of the second optical computing device 440b may provide the real-time concentration of hydrogen sulfide ($H_2S$) entrained in the drilling fluid 422 and may trigger an alarm when the registered level of the $H_2S$ surpasses a predetermined "safe" limit. In response to the alarm, $H_2S$ scavengers or other additives may be added to the drilling fluid 422 via the hopper 438 to remedy the situation.

Moreover, by comparing the measurements or resulting output signals 444a,b provided by the first and second optical computing devices 440a,b, respectively, an operator may be apprised as to the quantity and concentration of one or more gases that may have entered or otherwise become entrained in the drilling fluid 422 while circulating through the borehole 416. Such data may be useful in providing information as to the hydrocarbon content of the rock being drilled through.

In other embodiments, a third optical computing device 440c may be arranged in the flow line 430 following the degassing unit 433 (e.g., adjacent an outlet to the degassing unit 433). The third optical computing device 440c may be configured to provide a third output signal 444c indicative of the concentration of one or more gases in the drilling fluid 422 after the drilling fluid 422 has been processed in the degassing unit 433. In some embodiments, the output signals 440b,c may be conveyed to the signal processor 442 and a resulting output signal 446 from the signal processor 442 may provide the operator with a qualitative and/or quantitative comparison of the second and third output signals 440b,c, thereby providing valuable information as to the effectiveness of the degassing unit 433.

Depending on the resulting concentrations of gases reported by the second and third optical computing devices 440b,c, a determination may be made that the degassing unit 433 is operating efficiently or otherwise inefficiently. Upon being notified of ineffective or inefficient performance on the part of the degassing unit 433, the operator may then remedy the inefficiency by altering one or more operating parameters of the degassing unit 433. Parameters of the degassing unit 433 that may be adjusted may include, but are not limited to, increasing drilling fluid 422 agitation time, adjusting the temperature of the drilling fluid 422 within the degassing unit 433, adjusting the flow rate of the drilling fluid 422, adjusting the vacuum (e.g., such as on a vacuum-type degassing unit), and combinations thereof.

As will be appreciated, fine tuning the degassing unit 433 will ensure that the drilling fluids 422 are degassed at proper and efficient operating levels. In some embodiments, an automated control system (not shown) may be communicably coupled to both the signal processor 442 and the degassing unit 433. When the third output signal 444c surpasses a predetermined threshold for suitable drilling fluid 422, the automated control system may be configured to autonomously adjust the one or more operating parameters of the degassing unit 433.

In some cases, the operating parameters of the degassing unit 433 are not adjusted but instead the signal processor 442 may be configured to calculate an efficiency rating or correction factor for the degassing unit 433. Such a correction factor may be applied to subsequent mud logging gas analyses to correct for the quantity of gas remaining in the drilling fluid 422 at different depths in the borehole 416. In other words, the operating parameters of the degassing unit 433 may remain constant and instead the correction factor may be used to normalize the gas concentration results against prior tests such that an equal comparison of the data over time and across different drilled zones within the borehole 416 may be made. Moreover, since an efficiency rating may be calculated, this may allow the operator to make a calculation and correct the data so that it is normalized against how efficient the extraction process in the degassing unit 433 is.

In yet other embodiments, a fourth optical computing device 440d and a fifth optical computing device 440e may be included in the drilling assembly 400 and arranged in fluid communication with the annulus 426 of the borehole 416. In particular, the fourth optical computing device 440d may be arranged prior to or otherwise downhole from the wellbore choke valve 428, and the fifth optical computing device 440e may be arranged following the surface choke valve 434. As the drilling fluid 422 returns to the surface via the annulus 426, the wellbore choke valve 428 serves to regulate the elevated pressures that may be present in the downhole drilling environment, and the surface choke valve 434 may reduce the pressure and thereby deliver a lower pressure drilling fluid 422 that may safely be handled by rehabilitation devices for processing.

By reducing the pressure of the drilling fluid 422 across the surface choke valve 434, however, gases may release out of the drilling fluid 422. Accordingly, the second and fourth optical computing devices 440b,d may be advantageous in providing a real or near real-time concentration of one or more gases in the drilling fluid 422 as it circulates at or near actual downhole drilling environment conditions. The resulting output signals 444b,d from the second and fourth optical computing devices 440b,d, therefore, may be useful in mud logging gas analysis of the drilling fluid 422 at downhole operating conditions. The fifth optical control device 440e may be configured to provide an indication of the gas concentration in the drilling fluid 422 following the surface choke valve 434. By comparing the second/fourth output signals 444b,d with the fifth output signal 444e, an operator may be apprised of the quantity of gas that has released out of the drilling fluid 422 after the surface choke valve 428.

In yet other embodiments, one or more optical computing devices, as generally described herein, may be used to help facilitate a sampling process for traditional mud logging gas analysis operations. As illustrated, the drilling assembly 400 may further include a drilling fluid sampling system 448 used to undertake traditional mud logging gas analysis. In at least one embodiment, the sampling system 448 may be the EAGLE™ Gas Extraction System available through Halliburton Sperry Drilling of Houston, Tex., USA. In other embodiments, the sampling system 448 may be any other gas extraction and sampling system known to those skilled in the art for undertaking mud logging gas analysis of drilling fluids.

The sampling system 448 may be configured to receive a continuous supply of drilling fluid 422 as the drilling fluid 422 returns to the surface. For example, in at least one embodiment, sampling system 448 may be fluidly coupled to the annulus 426 via a second flow line 450. In at least one embodiment, the second flow line 450 may be a suction probe communicably coupled to the annulus 426 and configured to extract a regulated amount of drilling fluid 422 therefrom. The sampling system 448 may include or otherwise encompass a constant volume extractor (not shown) used to deliver a continuous constant volume of the drilling fluid 422 to a hermetic degassing chamber (not shown) while maintaining consistent gas extraction from the drilling fluid 422 within the degassing chamber.

Within the degassing chamber, the drilling fluid 422 may be heated to a constant temperature and agitated in order to break out any gases entrained within the sample drilling fluid 422. The degassed drilling fluid 422 may be returned to the mud pit 436 via a conduit 452 such that a continuous gas sampling system is facilitated. At the same time, the extracted gases may be monitored using a sixth optical computing device 440f in optical communication with the degassing chamber or a sample of the gas extracted from the drilling fluid 422. In real or near real-time, the sixth optical computing device 440f may be configured to provide an output signal 444f indicative of the type and concentration of one or more gases as extracted from the drilling fluid 422. The output signal 444f may be conveyed to the signal processor 442 for processing. Accordingly, the sixth optical computing device 440f may be added to and otherwise supplement traditional mud logging gas analysis techniques and provide quicker results.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments disclosed herein include:

A. A mud logging gas analysis system that includes a first optical computing device arranged at or near an outlet of the borehole and having a first integrated computational element configured to optically interact with the drilling fluid as it exits the borehole and generate a first output signal corresponding to a concentration of a gas present in the drilling fluid at the outlet of the borehole, wherein the drilling fluid circulates through a flow path into and out of the borehole during drilling operations, and a signal processor communicably coupled to the first optical computing device and configured to receive the first output signal and determine the concentration of the gas present in the drilling fluid at the outlet of the borehole.

B. A mud logging gas analysis system that includes a degassing unit fluidly coupled to a borehole and configured to receive drilling fluid from the borehole, the degassing unit having an inlet and an outlet, a first optical computing device arranged adjacent the inlet and having a first integrated computational element configured to optically interact with the drilling fluid before it enters the degassing unit and generate a first output signal corresponding to a concentration of a gas present in the drilling fluid before the degassing unit, a second optical computing device arranged adjacent the outlet and having a second integrated computational element configured to optically interact with the drilling fluid after exiting the degassing unit and generate a second output signal corresponding to the concentration of the gas present in the drilling fluid after the degassing unit, and a signal processor communicably coupled to the first and second optical computing devices and configured to receive the first and second output signals and provide a resulting output signal indicative of how the concentration of the gas changes between the inlet and the outlet of the degassing unit.

C. A method of conducting mud logging gas analysis that includes circulating a drilling fluid within a flow path that extends into and out of a borehole during drilling operations, generating a first output signal with a first optical computing device arranged at or near an outlet of the borehole, the first optical computing device having a first integrated computational element configured to optically interact with the drilling fluid, wherein the first output signal corresponds to a concentration of a gas present in the drilling fluid at the outlet, receiving the first output signal with a signal processor communicably coupled to the first optical computing device, and determining the concentration of the gas present in the drilling fluid at the outlet of the borehole with the signal processor.

D. A method of conducting mud logging gas analysis that includes conveying a drilling fluid through a degassing unit fluidly coupled to a borehole, the degassing unit having an inlet and an outlet, generating a first output signal with a first optical computing device arranged adjacent the inlet, the first optical computing device having a first integrated computational element configured to optically interact with the drilling fluid before it enters the degassing unit, wherein the first output signal corresponds to a concentration of a gas present in the drilling fluid before the degassing unit, generating a second output signal with a second optical computing device arranged adjacent the outlet, the second optical computing device having a second integrated computational element configured to optically interact with the drilling fluid after it exits the degassing unit, wherein the second output signal corresponds to the concentration of the gas present in the drilling fluid following the degassing unit, receiving the first and second output signals with a signal processor communicably coupled to the first and second optical computing devices, and generating a resulting output signal with the signal processor, the resulting output signal being indicative of how the concentration of the gas changes between the inlet and the outlet.

Each of embodiments A, B, C, and D may have one or more of the following additional elements in any combination: Element 1: wherein the gas is selected from the group comprising methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof. Element 2: further comprising a second optical computing device arranged at or near an inlet to the borehole and having a second integrated computational element configured to optically interact with the drilling fluid and generate a second output signal corresponding to the concentration of the gas present in the drilling fluid at the inlet to the borehole. Element 3: wherein the signal processor is communicably coupled to the second optical computing device and configured to receive the second output signal and calculate a difference between the first and second output signals and report how the concentration of the gas changed between the inlet and the outlet. Element 4: further comprising a wellbore choke valve arranged within the borehole at or near the outlet, and a second optical computing device arranged within the flow path downhole from the wellbore choke valve and having a second integrated computational element configured to optically interact with the drilling fluid and generate a second output signal corresponding to the concentration of the gas present in the drilling fluid downhole from the wellbore choke valve, wherein the signal processor is communicably coupled to the second optical computing device and configured to receive the second output signal and determine the concentration of the gas present in the drilling fluid downhole from the wellbore choke valve. Element 5: further comprising a third optical computing device arranged within the flow path uphole from the wellbore choke valve and having a third integrated computational element configured to optically interact with the drilling fluid and generate a third output signal corresponding to the concentration of the gas present in the drilling fluid uphole from the wellbore choke valve, wherein the signal processor is communicably coupled to the third optical computing device and configured to receive the third output signal and calculate a difference between the second and third output signals.

Element 6: further comprising an automated control system communicably coupled to the signal processor and configured to adjust one or more operating parameters of the degassing unit in response to the resulting output signal. Element 7: wherein the signal processor calculates a correction factor in view of the resulting output signal, the correction factor being used to normalize future gas concentration results in order to make an equal comparison of data over time and across different drilled zones within the borehole. Element 8: further comprising a drilling fluid sampling system fluidly coupled to the borehole and configured to receive a continuous sample supply of drilling fluid exiting the borehole, the drilling fluid sampling system having a hermetic degassing chamber configured to separate the gas from the sample supply of drilling fluid; a third optical computing device in optical communication with the hermetic degassing chamber and having a third integrated computational element configured to optically interact with gases extracted from the sample supply of drilling fluid and generate a third output signal corresponding to the concentration of the gases extracted from the sample supply of drilling fluid, wherein the signal processor is communicably coupled to the third optical computing device and configured to receive the third output signal and determine a concentration of the gases extracted from the sample supply of drilling fluid.

Element 9: further comprising generating a second output signal with a second optical computing device arranged at or near an inlet to the borehole, the second optical computing device having a second integrated computational element configured to optically interact with the drilling fluid, wherein the second output signal corresponds to the concentration of the gas present in the drilling fluid at the inlet, receiving the second output signal with the signal processor communicably coupled to the second optical computing device, and calculating a difference between the first and second output signals with the signal processor, the difference being indicative of how the concentration of the gas changed between the inlet and the outlet. Element 10: wherein a wellbore choke valve is arranged within the borehole at or near the outlet, the method further comprising generating a second output signal with a second optical computing device arranged within the flow path downhole from the wellbore choke valve, the second optical computing device having a second integrated computational element configured to optically interact with the drilling fluid, wherein the second output signal corresponds to the concentration of the gas present in the drilling fluid downhole from the wellbore choke valve, receiving the second output signal with the signal processor communicably coupled to the second optical computing device, and determining the concentration of the gas present in the drilling fluid downhole from the wellbore choke valve with the signal processor. Element 11: further comprising generating a third output signal with a third optical computing device arranged within the flow path uphole from the wellbore choke valve, the third optical computing device having a third integrated computational element configured to optically interact with the drilling fluid, wherein the third output signal corresponds to the concentration of the gas present in the drilling fluid uphole from the wellbore choke valve, receiving the third output signal with the signal processor communicably coupled to the third optical computing device, and calculating a difference between the second and third output signals with the signal processor.

Element 12: further comprising adjusting one or more operating parameters of the degassing unit in response to the resulting output signal. Element 13: wherein adjusting the one or more operating parameters of the degassing unit comprises adjusting the one or more operating parameters as directed by an automated control system communicably coupled to the signal processor. Element 14: further comprising calculating a correction factor with the signal processor in view of the resulting output signal, and applying the correction factor to future gas concentration results in order to normalize the future gas concentration results over time and across different drilled zones within the borehole. Element 15: further comprising providing a continuous sample supply of drilling fluid exiting the borehole to a drilling fluid sampling system fluidly coupled to the borehole, the drilling fluid sampling system having a hermetic degassing chamber, separating gases from the sample supply of drilling fluid with the hermetic degassing chamber, generating a third output signal with a third optical computing device in optical communication with the hermetic degassing chamber, the third computing device having a third integrated computational element configured to optically interact with the gases extracted from the sample supply of drilling fluid, wherein the third output signal correspond to a concentration of the gases extracted from the sample supply of drilling fluid, receiving the third output signal with the signal processor communicably coupled to the third optical computing device, and determining the concentration of the gases extracted from the sample supply of drilling fluid with the signal processor.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively described herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A system, comprising:
   a first optical computing device comprising a beamsplitter configured to separate a compensating beam and a signal beam from a sample light generated by a drilling fluid exiting a borehole, the first optical computing device comprising a first integrated computational element that optically interacts with the signal beam to generate a fluid interacted light, wherein:
   the first integrated computational element comprises a plurality of alternating layers of material, each alternating layer of material having a thickness selected so that an intensity of the fluid interacted light is proportional to a concentration of a gas present in the drilling fluid at or near an outlet of the borehole, and
   wherein the first optical computing device generates a first output signal corresponding to the intensity of the fluid interacted light and the drilling fluid circulates through a flow path into and out of the borehole during drilling operations;
   a detector configured to generate a compensating signal indicative of an intensity of the compensating beam, wherein the compensating signal comprises the first output signal and a radiative deviation of the fluid interacted light; and
   a signal processor communicably coupled to the first optical computing device and configured to:
   determine the concentration of the gas present in the drilling fluid at the outlet of the borehole by subtracting the first output signal from the compensating signal to normalize the first output signal, and
   provide a command to correct a drilling operation when the concentration of the gas present in the drilling fluid at the outlet of the borehole indicates an out of range reading.

2. The system of claim 1, wherein the gas is selected from the group consisting of methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof.

3. The system of claim 1, further comprising a second optical computing device arranged at or near an inlet to the borehole and having a second integrated computational element configured to optically interact with the drilling fluid and generate a second output signal corresponding to the concentration of the gas present in the drilling fluid at the inlet to the borehole.

4. The system of claim 3, wherein the signal processor is communicably coupled to the second optical computing device and configured to receive the second output signal and calculate a difference between the first and second output signals and report a change in the concentration of the gas between the inlet and the outlet.

5. The system of claim 1, further comprising:
   a wellbore choke valve arranged within the borehole at or near the outlet; and
   a second optical computing device arranged within a flow path downhole from the wellbore choke valve and having a second integrated computational element configured to optically interact with the drilling fluid and generate a second output signal corresponding to the concentration of the gas present in a drilling fluid downhole from the wellbore choke valve,
   wherein the signal processor is communicably coupled to the second optical computing device and configured to receive the second output signal and determine the concentration of the gas present in the drilling fluid downhole from the wellbore choke valve.

6. The system of claim 5, further comprising:
   a third optical computing device arranged within a flow path uphole from the wellbore choke valve and having a third integrated computational element configured to optically interact with the drilling fluid and generate a third output signal corresponding to the concentration of the gas present in a drilling fluid uphole from the wellbore choke valve,
   wherein the signal processor is communicably coupled to the third optical computing device and configured to receive the third output signal and calculate a difference between the second and third output signals.

7. A system, comprising:
   a degassing unit fluidly coupled to a borehole to receive a drilling fluid from the borehole, the degassing unit having an inlet and an outlet and being operable to heat the drilling fluid;
   a first optical computing device comprising a beamsplitter configured to separate a compensating beam and a signal beam from a sample light generated by a drilling fluid exiting a borehole, the first optical computing device comprising a first integrated computational element that optically interacts with the signal beam to generate a fluid interacted light, wherein:
   the first integrated computational element comprises a plurality of alternating layers of material, each of the plurality of alternating layers of material having a thickness selected so that an intensity of the fluid interacted light is proportional to a concentration of a gas present in the drilling fluid before the fluid enters the degassing unit, and wherein the first optical computing device generates a first output signal corresponding to the intensity of the fluid interacted light;

a second optical computing device arranged adjacent the outlet and having a second integrated computational element that optically interacts with the drilling fluid after the drilling fluid exits the degassing unit, wherein the second optical computing device generates a second output signal corresponding to the concentration of the gas present in the drilling fluid after the drilling fluid exits a degassing unit;

a detector configured to generate a compensating signal indicative of an intensity of the compensating beam, wherein the compensating signal comprises the first output signal and a radiative deviation of the fluid interacted light; and a signal processor communicably coupled to the first optical computing device and to the second optical computing device and configured to:

provide a resulting output signal indicative of a change in the concentration of the gas between the inlet and the outlet of the degassing unit by subtracting the first output signal from the compensating signal to normalize the first output signal, and provide a command to correct a drilling operation when the concentration of the gas present in the drilling fluid at the outlet of the borehole indicates an out of range reading.

8. The system of claim 7, wherein the gas is selected from the group consisting of methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof.

9. The system of claim 7, further comprising an automated control system communicably coupled to the signal processor and configured to adjust one or more operating parameters of the degassing unit in response to the resulting output signal.

10. The system of claim 7, wherein the signal processor calculates a correction factor in view of the resulting output signal, the correction factor being used to normalize future gas concentration results in order to make an equal comparison of data over time and across different drilled zones within the borehole.

11. The system of claim 7, further comprising:

a drilling fluid sampling system fluidly coupled to the borehole and configured to receive a sample supply of drilling fluid exiting the borehole, the drilling fluid sampling system having a hermetic degassing chamber configured to separate the gas from the sample supply of drilling fluid; and a third optical computing device in optical communication with the hermetic degassing chamber and having a third integrated computational element configured to optically interact with gases extracted from the sample supply of drilling fluid and to generate a third output signal corresponding to the concentration of the gases extracted from the sample supply of drilling fluid, wherein the signal processor is communicably coupled to the third optical computing device and configured to receive the third output signal and determine a concentration of the gases extracted from the sample supply of drilling fluid.

12. A method, comprising:

circulating a drilling fluid within a flow path that extends into and out of a borehole during drilling operations;

separating, with a beam splitter, a compensating beam and a signal beam from a sample light generated by the drilling fluid, generating a first output signal with a first optical computing device arranged at or near an outlet of the borehole, the first optical computing device having a first integrated computational element that optically interacts with the drilling fluid to generate a fluid interacted light having an intensity proportional to a concentration of a gas present in the drilling fluid at or near the outlet of the borehole, wherein the first output signal corresponds to the intensity of the fluid interacted light;

generating a compensating signal indicative of a radiative deviation of the fluid interacted light, wherein the compensating signal comprises the first output signal and the radiative deviation of the fluid interacted light;

receiving the first output signal and the compensating signal with a signal processor communicably coupled to the first optical computing device;

determining the concentration of the gas present in the drilling fluid at the outlet of the borehole with the signal processor by subtracting the first output signal from the compensating signal to normalize the first output signal; and adding an additive to the drilling fluid when the concentration of the gas exceeds a preprogrammed ranged of suitable operation for the drilling fluid.

13. The method of claim 12, further comprising:

generating a second output signal with a second optical computing device arranged at or near an inlet to the borehole, the second optical computing device having a second integrated computational element configured to optically interact with the drilling fluid, wherein the second output signal corresponds to the concentration of the gas present in the drilling fluid at the inlet;

receiving the second output signal with the signal processor communicably coupled to the second optical computing device; and calculating a difference between the first and second output signals with the signal processor, the difference being indicative of a change in the concentration of the gas between the inlet and the outlet.

14. The method of claim 12, wherein a wellbore choke valve is arranged within the borehole at or near the outlet, the method further comprising:

generating a second output signal with a second optical computing device arranged within a flow path downhole from the wellbore choke valve, the second optical computing device having a second integrated computational element configured to optically interact with the drilling fluid, wherein the second output signal corresponds to the concentration of the gas present in a drilling fluid downhole from the wellbore choke valve;

receiving the second output signal with the signal processor communicably coupled to the second optical computing device; and determining the concentration of the gas present in the drilling fluid downhole from the wellbore choke valve with the signal processor.

15. The method of claim 14, further comprising:
generating a third output signal with a third optical computing device arranged within a flow path uphole from the wellbore choke valve, the third optical computing device having a third integrated computational element configured to optically interact with the drilling fluid, wherein the third output signal corresponds to the concentration of the gas present in a drilling fluid uphole from the wellbore choke valve;
receiving the third output signal with the signal processor communicably coupled to the third optical computing device; and
calculating a difference between the second and third output signals with the signal processor.

16. A method, comprising:
conveying a drilling fluid through a degassing unit fluidly coupled to a borehole, the degassing unit having an inlet and an outlet and being operable to heat the drilling fluid;
separating, with a beam splitter, a compensating beam and a signal beam from a sample light generated by the drilling fluid;
generating a first output signal with a first optical computing device arranged adjacent the inlet, the first optical computing device having a first integrated computational element that optically interacts with the drilling fluid before the drilling fluid enters the degassing unit to generate a fluid interacted light having an intensity proportional to a concentration of a gas present in the drilling fluid before the drilling fluid enters the degassing unit, wherein the first output signal corresponds to the intensity of the fluid interacted light;
generating a second output signal with a second optical computing device arranged adjacent the outlet, the second optical computing device having a second integrated computational element that optically interacts with the drilling fluid after the drilling fluid exits the degassing unit, wherein the second output signal corresponds to the concentration of the gas present in the drilling fluid after the drilling fluid exits the degassing unit;
generating a compensating signal indicative of a radiative deviation of the fluid interacted light, wherein the compensating signal comprises the first output signal and the radiative deviation of the fluid interacted light;
receiving the first and second output signals and the compensating signal with a signal processor communicably coupled to the first optical computing device and the second optical computing device;
generating, with the signal processor, a resulting signal indicative of a change in the concentration of the gas between the inlet and the outlet by subtracting the first output signal from the compensating signal to normalize the first output signal; and
providing a command to correct a drilling operation when the change in the concentration of the gas between the inlet and the outlet indicates an out of range reading.

17. The method of claim 16, further comprising adjusting one or more operating parameters of the degassing unit in response to the resulting signal.

18. The method of claim 17, wherein adjusting the one or more operating parameters of the degassing unit comprises adjusting the one or more operating parameters as directed by an automated control system communicably coupled to the signal processor.

19. The method of claim 16, further comprising:
calculating a correction factor with the signal processor in view of the resulting signal; and
applying the correction factor to future gas concentration results in order to normalize the future gas concentration results over time and across different drilled zones within the borehole.

20. The method of claim 16, further comprising:
providing a sample supply of drilling fluid exiting the borehole to a drilling fluid sampling system fluidly coupled to the borehole, the drilling fluid sampling system having a hermetic degassing chamber;
separating gases from the sample supply of drilling fluid with the hermetic degassing chamber;
generating a third output signal with a third optical computing device in optical communication with the hermetic degassing chamber, the third optical computing device having a third integrated computational element configured to optically interact with the gases extracted from the sample supply of drilling fluid, wherein the third output signal corresponds to a concentration of the gases extracted from the sample supply of drilling fluid;
receiving the third output signal with the signal processor communicably coupled to the third optical computing device; and
determining the concentration of the gases extracted from the sample supply of drilling fluid with the signal processor.

* * * * *